United States Patent [19]

Stoker

[11] Patent Number: 4,865,997

[45] Date of Patent: Sep. 12, 1989

[54] ASSAY FOR LIGANDS BY SEPARATING BOUND AND FREE TRACER FROM SAMPLE

[75] Inventor: Ronald L. Stoker, Bountiful, Utah

[73] Assignee: Becton Dickinson and Company, Franklin Lakes, N.J.

[21] Appl. No.: 582,953

[22] Filed: Feb. 23, 1984

[51] Int. Cl.$^4$ .......................................... G01N 33/538
[52] U.S. Cl. ..................................... 436/541; 436/538; 436/546; 436/548; 436/824
[58] Field of Search ............... 436/538, 541, 548, 536, 436/542, 546, 824; 435/7, 803, 804, 824

[56] References Cited

U.S. PATENT DOCUMENTS

| 4,022,577 | 5/1977 | Brooker et al. ................... 23/230 B |
| 4,268,494 | 5/1981 | Reese . |
| 4,376,110 | 3/1983 | David . |

Primary Examiner—Robert J. Hill, Jr.
Attorney, Agent, or Firm—Elliot M. Olstein; John N. Bain; John G. Gilfillan

[57] ABSTRACT

In an assay wherein there is produced in an assay sample tracer bound to a soluble binder and unbound tracer, both bound and unbound tracer are separated from the assay sample for separate determination thereof by use of a supported binder for the soluble binder and a supported binder for the tracer. The assay may be effected as a "flow-through assay" by causing the sample to flow through successive chambers containing the supported binders.

14 Claims, No Drawings

ASSAY FOR LIGANDS BY SEPARATING BOUND AND FREE TRACER FROM SAMPLE

This invention relates to an assay, and products used in such assay. More particularly, this invention relates to an assay for either a hapten, antigen or antibody.

Assays for various ligands in a sample (analyte) are known in the art. In one type of assay, the analyte and a labeled form of the analyte (tracer) compete for a limited number of binding sites on a binder (for example, an antibody) which is specific for the tracer and analyte. The amount of tracer which becomes bound to the binder is inversely proportional to the amount of analyte in the sample. The tracer which is bound to the binder (bound portion) is separated from the tracer which is not bound to the binder (free portion), and the amount of analyte in the sample may be determined by measuring the amount of tracer in either the bound and/or free portion by use of a standard curve generated by use in the assay of samples containing known amounts of analyte.

In many cases, the sample containing the analyte to be assayed includes materials which may interfere with the ability to determine the amount of tracer in the free tracer portion which remains in the sample. Thus, for example, in an assay employing a tracer containing a fluorescent label, a serum sample which contains the analyte generally includes background fluorescence. Such background fluorescence may interfere with the ability to properly determine the amount of tracer which remains as the free portion in the serum sample. This can interfere with the accuracy and precision of the assay.

In accordance with one aspect of the present invention, there is provided an improvement in an assay for an analyte in a sample wherein in the assay procedure there is produced in the sample a mixture of tracer bound to a soluble binder (bound tracer) and tracer which is not bound to the binder (free tracer). In accordance with one aspect of the present invention, the sample containing the mixture of bound and free tracer is contacted with a first supported binder, followed by separating the sample from the first supported binder, contacting the separated sample with a second supported binder, and separating sample from the second supported binder, wherein one of the first and second supported binder is a binder for the tracer and the other of the first and second supported binder is a binder for the soluble binder, whereby both bound and free tracer are separated from the sample. In this manner, both the bound and free tracer may be determined apart from the sample, with a determination of at least one of the separated bound and free tracer, preferably both, being used as a measure of analyte in the sample.

More particularly, in accordance with one assay procedure, the sample containing the analyte is incubated with tracer and a soluble binder for the tracer to produce a mixture of free tracer and tracer bound to the soluble binder. The incubated sample is then contacted with a first binder supported on a solid support, which first binder is a binder for the soluble binder, to thereby bind the complex of tracer bound to the soluble binder. In this manner, bound tracer is removed from the sample. Subsequently, after separation of the sample from the supported first binder, the sample is contacted with a second binder supported on a solid support, which second binder is a binder for the tracer, whereby the free tracer which remains in the sample becomes bound to the second supported binder. After separation of the sample from the second supported binder, the amount of tracer in the bound fraction (the tracer bound to the first supported binder through the soluble binder) and the free tracer (the tracer directly bound to the second supported binder) may be determined as a measure of analyte in the sample. Thus, for example, the bound tracer and the free tracer may be eluted from the first supported binder and the second supported binder, respectively, in order to determine the respective amounts of tracer.

Alternatively, in the above procedure, the sample may be initially contacted with the second supported binder and then contacted with the first supported binder.

In accordance with another procedure, the assay of the present invention may be employed for determining an antigen which has multiple determinant or binding sites. In such an assay procedure, a sample containing the antigen having multiple binding sites (analyte) is contacted with a tracer in the form of a binder for such antigen which has been labeled with an appropriate marker. As a result of such contact, the sample includes bound tracer (a complex of the labeled binder bound to the antigen) and free tracer (labeled binder which is not bound to the antigen).

The mixture is then contacted with a first supported binder which is a binder for the antigen whereby the bound tracer (complex of the antigen bound to the labeled binder) becomes bound to the first supported binder. The sample is then separated from the first supported binder, and such separated sample is then contacted with a second supported binder which is a binder for the labeled binder used in the assay, whereby the free tracer (unbound labeled binder from the incubated sample) becomes bound to the second supported binder. In this manner, both free tracer, and bound tracer, are separated from the sample. The free tracer and bound tracer may then be determined as a measure of the analyte (antigen having multiple binding sites) in the sample.

In accordance with one particularly preferred embodiment, the tracer is a labeled monoclonal antibody for one of the determinant or binding sites of the antigen; one of the first and second supported binder is the antigen (analyte) or appropriate analog thereof (preferably the first supported binder), and the other of the first and second supported binder is a monoclonal antibody for the other determinant or binding site of the antigen. In such an embodiment, the free tracer (unbound labeled monoclonal antibody) is separated from the sample by being bound to the supported analyte (or supported appropriate analog thereof) and the bound tracer (complex of labeled monoclonal antibody bound to the analyte) is separated from the sample by binding of the complex to the supported monoclonal antibody for the other determinant site of the antigen. In this manner, both the bound tracer and the free tracer are separated from the assay sample, and can be determined separately from the assay sample.

Thus, as should be apparent from the above, the present invention is applicable to a variety of assay techniques, provided that the bound tracer and the unbound tracer formed in the assay (free tracer) are each separately bound to a supported binder, with one of the first and second binders functioning to bind the bound tracer, and the other of the first and second supported binders functioning to bind the free tracer, whereby the proportions of bound and free tracer formed in the assay can be determined in a separate environment independently from the assay environment.

In the assay of the present invention, the first and second binders which are supported on a solid support are determined by the assay procedure. Thus, for example, if the first binder is specific for an antigen or a hapten (whether present as a bound complex, or in a free state), the binder may be a naturally occurring binder or an antibody to such antigen or hapten. If the first or second supported binder is a binder which is to be specific for an antibody, then such binder may be either an antigen or hapten which si immunospecific for the antibody, or an antibody elicited in response to the antibody to be bound, or a substance specific for the antibody, such as for example, protein A which selectively binds Fc fragments of antibodies. The selection of a suitable binder for use as the first and second supported binders in the assay of the present invention is deemed to be within the scope of those skilled in the art from the teachings herein.

The first and second supported binders may be prepared by supporting the binders on a wide variety of solid supports which are not soluble in the assay media. The solid supports employed for each of the binders may be different or the same support. As known in the art, such supports, include suitable polymers, such as polystyrene, polyethylene, polypropylene, polytetrachlorethylene, polyamides, polyacrylamines, cross-linked agarose, dextran, etc.; glass, bacterial cells, ion exchange resins; cotton, as described in U.S. Pat. No. 4,200,625, and supports of the type described in U.S. Pat. No. 4,059,685, etc. The scope of the present invention is not limited to any particular type of support, and the selection of a suitable support for use in supporting the first and second binders is deemed to be within the scope of those skilled in the art from the teachings herein.

Similarly, methods for supporting the binders on the solid support are generally known in the art, and the present invention is not limited to any technique for supporting the binder on a solid support. Thus, for example, as known in the art, binders may be supported on a solid support by adsorption, covalent coupling, etc.

Similarly, the support may be in a wide variety of forms, including solid particles, test tubes, solid sheets, etc. In accordance with a particularly preferred embodiment, each of the first and second supported binders are supported on a solid support in the first and second flowthrough chambers, whereby, the sample may be caused to flow sequentially through the first and second chambers containing the first and second supported binders. A representative example of a suitable flowthrough chamber is described in U.S. Pat. No. 4,059,685.

The tracer which is employed in the assay is dependent upon the analyte to be determined in the procedure. Thus, for example, if the analyte is an antigen, the tracer may be either an antibody labeled with a suitable marker or the antigen or appropriate analog of the antigen (appropriate analog means that the analog is bound by the binder for the antigen) labeled with a suitable marker. If the analyte is a hapten, then the tracer may be the hapten or appropriate analog thereof labeled with a suitable marker. If the analyte is an antibody, the tracer may be the appropriate antigen or hapten binding partner labeled with a suitable marker, or an antibody elicited in response to the analyte labeled with a suitable marker.

The marker which is used in producing the tracer may be any one of a wide variety of markers, including radioactive markers, absorbing dye markers, fluorescent markers, enzyme markers, chemiluminescent markers, etc. Such markers are known in the art, and the methods for conjugating such markers to the ligand portion of the tracer are also known in the art.

The present invention has particular applicability to assays in which the marker used for producing the tracer is a fluorescent marker in that background fluorescence of serum samples has caused particular problems in assays employing fluorescent tracers.

The soluble binder which is used in the assay is also dependent upon the analyte to be determined. As with the supported binders, the selection of unsupported binder (soluble binder), where appropriate, for producing bound tracer as well as unbound tracer, in the sample which is sequentially contacted with the first and second supported binder, is deemed to be within the scope of those skilled in the art from the teachings herein.

In accordance with a preferred embodiment of the present invention, the first and second supported binders are regenerated for reuse in the assay by eluting therefrom the material bound during the assay procedure. In this respect, such elution is accomplished by use of a suitable eluting liquid which is caused to flow over the first and second binders to elute the bound material without destroying the binding capacity of the supported binder. The use of such eluting liquids for regenerating binders (whether the material bound is an antigen, hapten or antibody), is generally known in the art and, therefore, the selection of a suitable eluting liquid is deemed to be within the scope of those skilled in the art from the teachings herein.

Although the present invention is also applicable to assay procedures wherein the binder is not regenerated for reuse in the assay, the invention has particular applicability to an assay wherein the first and second binders may be reused, and in particular, for use in an automated assay.

In accordance with a specific procedure employing a fluorescent tracer in an assay for an analyte which is either an antigen or hapten, wherein the supported binders are reused, the sample containing the analyte (antigen or hapten) is incubated with a soluble binder for the analyte (generally an antibody) and a fluorescent tracer which is the analyte or appropriate analog thereof labeled with a fluorescent marker. As a result of the incubation, the tracer and analyte compete for available binding sites on the binder, and there is produced a mixture which contains bound tracer (tracer complexed with the antibody) and unbound or free tracer (tracer which has not complexed with the antibody). The amount of bound tracer is inversely proportional to the amount of analyte in the sample.

After the incubation, the incubated sample is caused to flow through a chamber which includes a first binder supported on a solid support. The first binder may be a binder for the free tracer in the incubated sample. Alternatively, the first binder may be a binder for the antibody in the incubated sample, whereby bound tracer becomes bound to the first binder.

In the case where the binder in the first chamber is a binder for the analyte, the free tracer in the incubated sample becomes bound to the first binder supported in the first chamber. The sample which flows through the first chamber contains bound tracer in that in the first chamber only free tracer becomes bound to the supported binder, and such remaining sample is caused to flow through a second chamber containing a supported binder, which binder is a binder for the soluble antibody used in the incubation step. In the second chamber, the bound tracer is removed from the sample in that the complex of tracer bound to the soluble antibody becomes bound to the supported second binder as a result of binding of the antibody portion of the complex. The binder in the second chamber may be an antibody elicited in response to the soluble antibody used in the assay. In this manner, bound tracer is removed from the sample in the second chamber.

Subsequently, an elution liquid is passed through each of the first and second chambers, individually, so as to elute from the respective binders the free tracer and the bound tracer, with the eluted free tracer and the eluted bound tracer being separately passed to a suitable detector for measurement of the free and bound fractions. Subsequently, a suitable liquid may be passed through the chambers for permitting reuse of such chambers.

In this manner, each of the bound and free tracer fractions may be measured free of interfering substances which may be present in the serum sample. In addition, two different data points can be obtained so as to permit plotting of an appropriate ratio, such as the ratio of the bound fraction to the free fraction and/or the ratio of the bound fraction to the total tracer or some other method which would permit construction of a standard curve, and use of a standard curve for determining the concentration of the analyte in an unknown sample.

In accordance with another specific procedure employing a fluorescent tracer in an assay for a multi-site antigen (antigen having more than one determinant site), the sample containing or suspected of containing the multi-site antigen (analyte) is incubated with a tracer in the form of a labeled binder for the analyte (in particular, a labeled antibody for the analyte, which may be a labeled monoclonal antibody for one of the determinant sites), with the antibody being labeled with a fluorescent material. As a result of the incubation, a portion of the fluorescent tracer becomes bound to the analyte thereby producing a mixture of bound tracer (tracer complex with the analyte) and free tracer, with the amount of bound tracer being proportional to the amount of analyte in the sample.

After the incubation, the incubated sample is caused to flow through a chamber which includes a first binder on a solid support. In the case where the tracer is other than a fluorescent labeled monoclonal antibody, the first binder is a binder for the analyte whereby the complex of tracer bound to the analyte becomes bound to the first binder. In the case where the tracer is formed from a monoclonal antibody for one of the determinant sites of the antigen to be assayed, the first binder may be either the analyte or appropriate analog thereof, or the monoclonal antibody for the other determinant site of the analyte. In the case where the first binder is the analyte or appropriate analog thereof, then the free tracer becomes bound to the first supported binder. In the case where the first supported binder is a monoclonal antibody for the other determinant site of the analyte, the complex of tracer and analyte is bound to the first supported binder.

The remaining portion of the sample is caused to flow through a second chamber containing a second supported binder, which second supported binder is a binder for the portion of the tracer which is not bound to the first supported binder. In the case where the first supported binder is a binder for the analyte so as to bind the complex of tracer bound to the analyte, the second supported binder is a binder for the fluorescent labeled antibody; for example, the analyte or appropriate analog thereof, to thereby separate the free tracer from the sample. In the case where the first binder is the analyte or appropriate analog thereof, then the second supported binder is a monoclonal antibody for the other determinant site of the analyte. In the case where the first supported binder is a monoclonal antibody for the other determinant site of the analyte, the second supported binder is the analyte or appropriate analog thereof so as to bind the fluorescent labeled monoclonal antibody employed as a tracer.

Subsequently, an elution liquid is passed through each of the first and second chambers, individually, so as to elute from the respective binders the free tracer and the bound tracer, which are separately passed to an appropriate detector for measurement of the free and bound fractions.

As previously described, each of the bound and free tracer fractions may be measured free of interfering substances which may be present in the serum sample.

In accordance with a further aspect of the present invention, there is provided a suitable reagent kit or package for accomplishing an assay in accordance with the invention, with such kit or package including as principal components: (a) a first binder supported on a solid support, which binder is specific for the free tracer fraction produced in an assay; and (b) a second supported binder, supported on a solid support, which is different than the first binder, and which is specific for the bound tracer fraction produced in the assay (tracer complexed with soluble binder in a competition type of assay and tracer complexed with analyte in a sandwich type of assay). In accordance with the preferred embodiment, the supported first binder is within a flow-through chamber, and the supported second binder is in a flowthrough chamber.

The reagent kit or package also includes a tracer for the analyte to be determined. The tracer is generally a fluorescent labeled ligand. The reagent kit or package may also include suitable buffers, eluting liquids, appropriate wash liquids, standards, and the like. Various components, where applicable, are included in the reagent kit or package in separate containers; for example, vials. It is also to be understood that one or more of such materials may be packaged separately and independently from the reagent kit or packaged and sold as a separate item. Thus, for example, the first and second flowthrough chambers containing the first and second binders supported on a solid support may be each separately packaged from the other reagents and sold as a separate reagent kit or package.

The assay of the present invention may be employed for determining a wide variety of ligands, and has particular applicability to those ligands which are present in a sample, and in particular, the serum sample, in low concentrations in that the procedure significantly improves the ability to detect low concentrations of analyte in a sample by determining both bound and free tracer fractions independently of the sample which contains the analyte to be determined. Thus, for example, as representative examples of suitable ligands which can be determined in accordance with the procedure of the present invention, there may be mentioned human thyroid stimulating hormones; HCG; FSH; LH; insulin; CEA; ferritin; hepatitis associated antigens A and B; growth hormones; T4, T3, digoxin, cortisol, estriol, various drugs; e.g., theophylline, gentamicin, etc., and the like.

The invention will be further described with respect to the following example; however, the scope of the invention is not to be limited thereby;

EXAMPLE

A serum sample of digoxin is added to a solution of fluoresceindigoxin, hereafter referred to as a tracer. Rabbit anti-digoxin is added to this solution and is allowed to incubate for 10 minutes. The solution is then flowed over rabbit anti-digoxin supported on a solid support. The labeled and unlabeled digoxin, that was bound to the soluble rabbit and tracer become bound to the rabbit anti-digoxin binder. The remainder of the solution continues to flow until it reaches the second binder which is composed of goat and anti-rabbit antibodies supported on a solid support. The soluble antibodies, some of which are bound to tracer, are absorbed onto the second immunoabsorbent. The remainder of the sample continues to flow through to a waste receptacle. The entire system is then rinsed to remove any contaminants.

At this time, an elution buffer is passed through each chamber individually by means of a valve positioned between the two chambers. The first chamber releases labeled antigen which flows to a detector and is measured. This measurement is defined as "cup free". The second chamber releases the labeled and unlabeled digoxin, as well as the soluble antibody from the binder. The tracer is flowed to the detector and is measured and labeled as the "cup bound" fraction.

The present invention is particularly advantageous in that it permits measuring of both bound and free tracer in an assay separate from the sample containing the analyte to be determined. In this manner, the bound and free tracer fractions may be more accurately determined in that such bound and free tracers are determined free of any interfering substances which may be present in the sample. This is of particular advantage in a fluorescent assay wherein serum samples often have high amounts of background fluorescence which interfere with the ability to determine low amounts of tracer in such serum samples.

Another advantage of the present invention is that the percentage of analyte which is bound to soluble antibody can be quantitated in that a total value of tracer (free and bound) is directly determined.

Numerous modifications and variations of the present invention are possible in light of the above teachings and, therefore, within the scope of the appended claims, the invention may be practiced otherwise than as described.

What is claimed is:

1. An assay for analyte in a sample wherein there is produced in the sample a mixture containing a complex of tracer bound to a member selected from the group consisting of a soluble binder for the analyte and free tracer wherein said tracer is a labelled ligand and said ligand of the tracer is specifically bound by said member, the improvement comprising:

contacting sample containing the mixture of the complex and the free tracer with a first supported binder; contacting separated sample with a second supported binder; separating sample from the second supported binder, one of the first and second supported binders being a binder specific for the free tracer and the other of the first and second supported binders being a binder specific for said member of the complex to thereby separate both the complex and the free tracer from the sample; eluting the separated complex and the separated free tracer from the first and second supported binders; and determining the tracer portion of the eluted separated complex and the eluted separated free tracer as a measure of analyte.

2. The assay of claim 1 wherein the tracer is a fluorescent labeled ligand.

3. The assay of claim 2 wherein the first and second binders are supported on a solid support in first and second flowthrough chambers, and the sample sequentially flows through the first and second chambers.

4. The assay of claim 1 wherein the complex is tracer bound to a soluble binder for the analyte.

5. The assay of claim 4 wherein the soluble binder is an antibody.

6. The assay of claim 5 wherein the tracer is a fluorescent labeled ligand.

7. The assay of claim 6 wherein one of the first and second supported binders is a binder for the soluble antibody and the other is a binder for the tracer.

8. The assay of claim 1 wherein the complex is tracer bound to the analyte and said analyte is an antigen having multiple determinant sites.

9. The assay of claim 8 wherein the tracer is a fluorescent labeled antibody for the analyte.

10. The assay of claim 9 wherein the first supported binder is a binder for the analyte and the second supported binder is a binder for the tracer.

11. The assay of claim 8 wherein the tracer is a fluorescent labeled monoclonal antibody for one determinant site of the analyte, one of the first and second supported binder is a monoclonal antibody for another determinant site of the analyte, and the other of the first and second supported binder is analyte.

12. In a assay for an analyte selected from the group consisting of antigens and haptens in a serum sample, the improvement comprising:

contacting the serum sample containing analyte with a soluble antibody for the analyte and a tracer comprising ligand (bound by said soluble antibody) labeled with a fluorescent label, said ligand portion of the tracer being bound by said soluble antibody, to produce a complex of tracer bound to the soluble binder, said sample further containing free tracer; contacting said sample with a first supported antibody; separating sample from the first supported antibody; contacting separated sample with a second supported antibody; one of said first and second supported antibody being an antibody for the analyte and the ligand of tracer and the other of said first and second antibody being an antibody for the soluble antibody portion of the complex whereby the free tracer is separated from the sample by binding to one of the first and second antibody and the complex is separated from the sample by binding of the soluble antibody portion of the complex to the other of the first and second antibody; and separately determining separated tracer of the complex and separated free tracer as a measure of analyte.

13. In an assay for an analyte selected from the group consisting of antigens and haptens in a serum sample, the improvement comprising:

contacting the serum sample containing analyte with a soluble antibody for the analyte and a tracer comprising ligand labelled with a fluorescent label, said ligand portion of the tracer being bound by said soluble antibody, to produce a complex of a tracer bound to the soluble binder, said sample further containing free tracer; contacting said sample with a first supported antibody; separating sample from the first supported antibody; contacting separated sample with a second supported antibody; one of said first and second supported antibody being an antibody for the analyte and the ligand of tracer and the other of said first and second antibody being an antibody for the soluble antibody portion of the complex whereby the free tracer is separated from the sample by binding to one of the first and second antibody and the complex is separated from the sample by binding of the soluble antibody portion of the complex to the other of the first and second antibody; eluting the complex and free tracer from the first and second antibodies; and separately determining separated tracer of the eluted complex and separated eluted free tracer as a measure of analyte.

14. The assay of claim 13 wherein the first and second supported antibody are supported in first and second flowthrough chambers.